United States Patent [19]

Salo et al.

[11] Patent Number: 5,728,140
[45] Date of Patent: Mar. 17, 1998

[54] METHOD FOR EVOKING CAPTURE OF LEFT VENTRICLE USING TRANSEPTAL PACING LEAD

[75] Inventors: Rodney W. Salo, Fridley, Minn.; Angelo Auriccho, Magdeburg, Germany

[73] Assignee: Cardiac Pacemakers, Inc., St. Paul, Minn.

[21] Appl. No.: 664,740

[22] Filed: Jun. 17, 1996

[51] Int. Cl.⁶ .................................................. A61N 1/362
[52] U.S. Cl. ......................................................... 607/9
[58] Field of Search ............................. 607/126, 127, 607/9, 131, 28

[56] References Cited

U.S. PATENT DOCUMENTS

| | | |
|---|---|---|
| 4,928,688 | 5/1990 | Mower . |
| 5,334,222 | 8/1994 | Salo et al. . |
| 5,374,287 | 12/1994 | Rubin . |
| 5,476,502 | 12/1995 | Rubin . |
| 5,487,758 | 1/1996 | Hoegnelid et al. ............ 607/123 |
| 5,545,201 | 8/1996 | Helland et al. ............ 607/127 |

*Primary Examiner*—Scott M. Getzow
*Attorney, Agent, or Firm*—Haugen and Nikolai, P.A.

[57] ABSTRACT

A method and an apparatus for pacing the left ventricle of the heart includes the installation of a pacing electrode within the interventricular septum proximate the left ventricular wall thereof and then connecting the electrode to a source of electrical stimulating pulses. The electrode preferably comprises one and possibly two distalmost convolutions on an otherwise insulated corkscrew-style positive fixation lead.

5 Claims, 4 Drawing Sheets

METHOD FOR EVOKING CAPTURE OF LEFT VENTRICLE USING TRANSEPTAL PACING LEAD

BACKGROUND OF THE INVENTION

I. Field of the Invention

This invention relates generally to the treatment of congestive heart failure (CHF) using electrical stimulation to optimize hemodynamic performance of a sick heart, and more particularly to a method of providing stimulation to the left ventricle without a need for implanting a pacing lead in the left ventricular chamber.

II. Discussion of the Prior Art

As is explained in my earlier U.S. Pat. 5,334,222, only recently has it been recognized that patients with CHF can be made to exhibit improved hemodynamic performance by using electrical stimulation to optimize systolic and diastolic function.

The Mower U.S. Pat. No. 4,928,688 describes an arrangement for achieving bi-ventricular pacing in which electrical stimulating pulses are applied, via electrodes on separate pacing leads, to both the right and left ventricular chambers so as to obtain a coordinated contraction and pumping action of the heart.

While it is relatively safe to insert a pacing lead and associated electrode(s) into the right ventricle, there is a reluctance to installing a similar lead into the left ventricle because of a danger to the patient due to the possibility of a thrombus being generated which might result in an ischemic episode. Thus, in those incidences where left heart stimulation is desired, it has been a common practice to use an intercostal approach using a endocardial screw-in positive fixation lead. This entails entering the plural cavity with attendant risk of infection. It must be done under general anesthesia which carries its own risks, especially in the CHF patient population.

Accordingly, a need exists for a way of selectively pacing the right and left ventricles to achieve a desired synchronization, but which is less traumatic and better tolerated by CHF patients than known prior art techniques.

SUMMARY OF THE INVENTION

In order to selectively and independently capture and pace the left ventricle of a person's heart without the need for the placement of a pacing lead within the left ventricle itself, there is provided a pacing lead having a tissue-piercing, positive-fixation tip that may be routed through the superior vena cava and the tricuspid valve into the right ventricular chamber. By advancing the tissue piercing, positive-fixation tip into the interventricular septum until an electrode surface on the positive-fixation tip closely approaches, but does not penetrate, the left ventricular wall of the septum, it is possible to deliver cardiac stimulating pulses to capture and cause contraction of the left ventricle independently of the right ventricle.

In accordance with the present invention, the positive-fixation tip comprises a rigid helix similar to a corkscrew that has a proximal portion thereof coated with insulation but whose distal convolution(s) are bare and form an electrode surface. In a first embodiment, the corkscrew tip is of a predetermined length so that when it is fully screwed into the right ventricular septal wall, only the short distal length of the corkscrew that is not coated with insulation approaches, but does not penetrate, the left ventricular septal wall. When a pacemaker pulse generator applies electrical pulses to the lead, only the myocardial tissue of the left ventricle is immediately stimulated to evoke a contraction of the left ventricle.

In accordance with a further feature of the invention, a second electrode electrically insulated from the electrode surface on the corkscrew tip can be made to abut the right ventricular septal wall when the positive-fixation, corkscrew tip is in its fully advanced position. By connecting the second electrode by an elongated, flexible conductor to a terminal pin on the proximal end thereof, when the lead is appropriately connected to a pacemaker pulse generator, separate or simultaneous stimulation of both the right and left ventricles can be achieved. The cork-screw tip electrode may also be extendable and retractable relative to the lead body by rotating the conductor to which it is affixed. Stimulating pulses are applied as the tip electrode is screwed into the septal tissue and further advancement is terminated when it is sensed that left ventricular depolarization is occurring prior to right ventricular depolarization.

DESCRIPTION OF THE DRAWINGS

The foregoing features, objects and advantages of the invention will become apparent to those skilled in the art from the following detailed description of a preferred embodiment, especially when considered in conjunction with the accompanying drawings in which like numerals in the several views refer to corresponding parts.

DESCRIPTION OF THE PREFERRED EMBODIMENT

Figure 1:
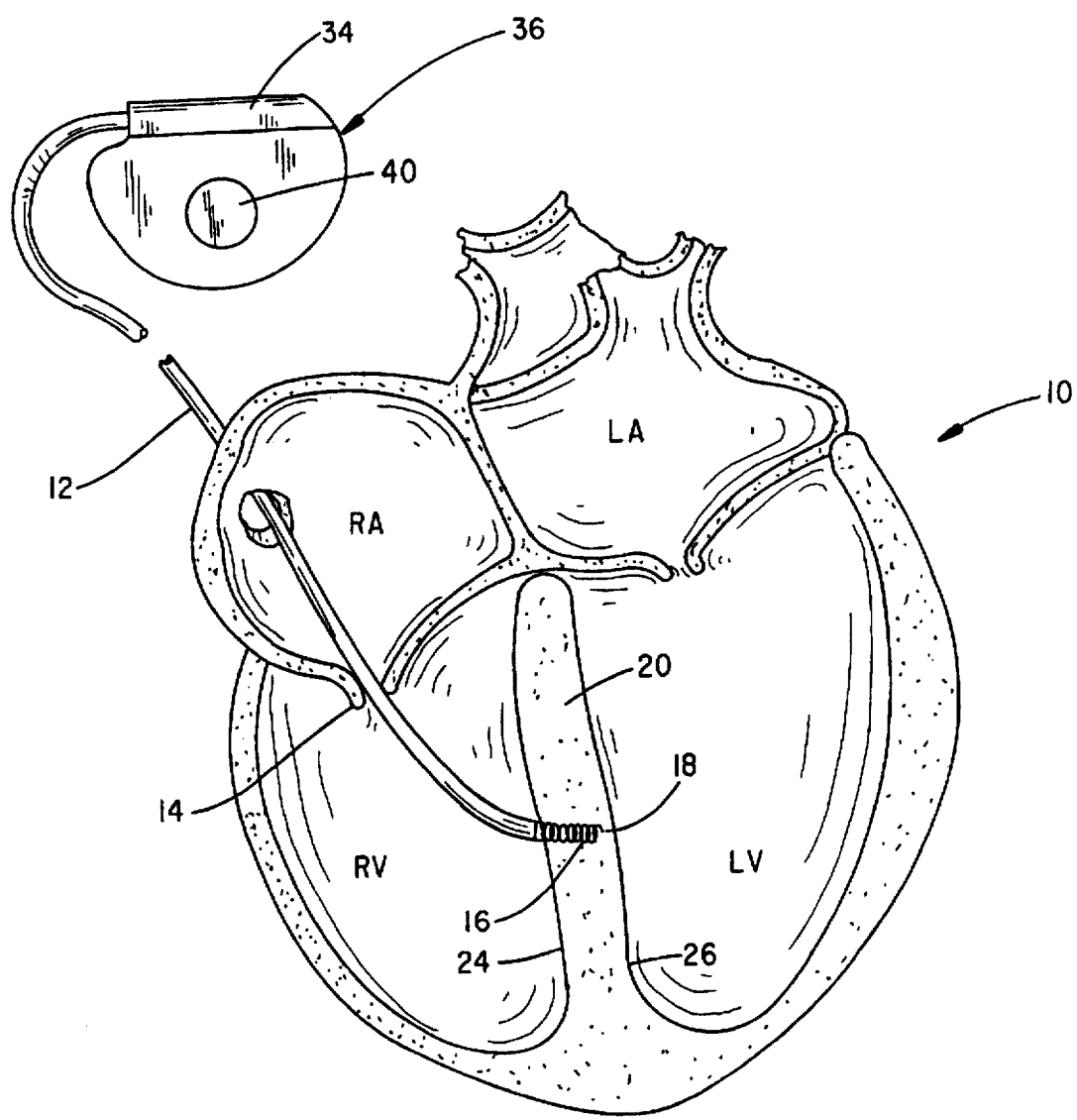
FIG. 1 is a cross-sectional view through the heart and showing the placement of a pacing lead for effecting capture and stimulation of the left ventricle.
Figure 2:
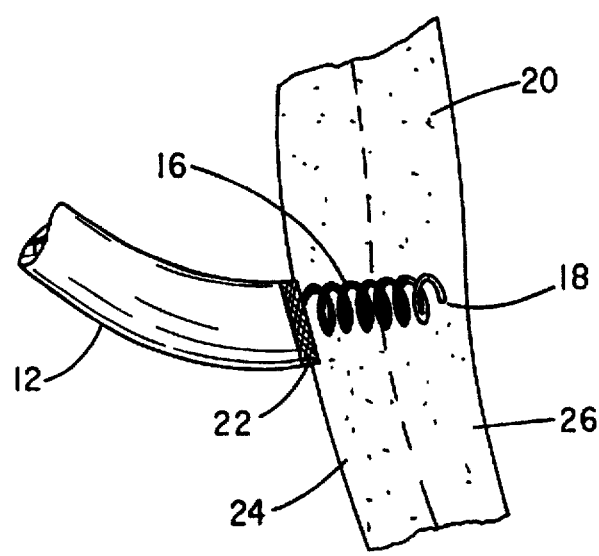
FIG. 2 is an enlarged partial view of FIG. 1 illustrating the manner in which a corkscrew-type, positive-fixation lead with an uninsulated conductive tip zone may be positioned in the septum for evoking left ventricular capture.

Referring to FIG. 1, there is shown a cross-sectional view taken through the heart 10 and showing a pacing lead 12 extending through the right atrium RA and through the tricuspid valve 14 into the right ventricle RV. As shown in the enlarged partial view of FIG. 2, the lead 12 has a conductive, relatively rigid helix 16 at the distal end thereof which terminates in a tissue-piercing tip 18. In FIGS. 1 and 2, the rigid helix is shown as being screwed into the interventricular septum 20 to positively fix the lead in place.

With continued reference to FIG. 2, it is seen that all but a predetermined number of convolutions of the helix have their surface coated with an insulating layer and only the most distal convolutions are free of insulation and thereby function as a tissue stimulating surface or electrode. The overall length of the rigid helix 16 is such that when the distal end 22 of the lead body 12 is abutting the right ventricular septal wall 24, the tissue piercing tip 18 and uninsulated distal convolutions are located within the myocardial tissue lying just inward of the left ventricular septal wall 26. Stated otherwise, the length of the helix 16 is such that when advanced into the interventricular septum, the tissue piercing tip 18 does not penetrate through the left ventricular wall surface 26 of the septum. With no limitation intended, the helical tip may have a length of about 5 to 8 mm and the uninsulated tip portion may be 1 to 2 mm in length. To increase the surface area of the uninsulated tip, it may be coated with a porous conductive material as is known in the art.

Figure 3:
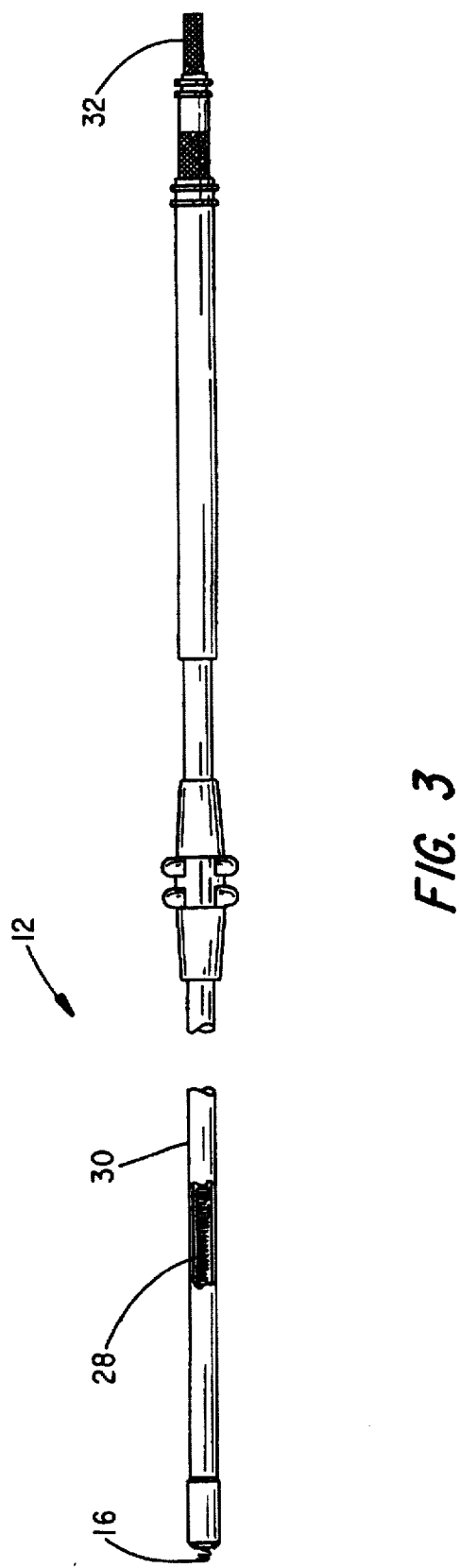
FIG. 3 is a side elevational view of a pacing lead constructed in accordance with the present invention.

As is shown in the side elevational view of FIG. 3, the pacing lead 12 may comprise an elongated flexible conductor 28 that is covered by a flexible, body-compatible, fluid-impervious, plastic sheath 30. The conductor 28 has its distal end conductively connected to the helix 16 and its proximal end conductively connected to a terminal pin 32, which is adapted to cooperate with contacts within the header 34 (FIG. 1) of a cardiac stimulating device 36. The lead illustrated in FIG. 3 may comprise a Type UNI4169 pacing lead available from CPI/Guidant Corporation, except that the positive fixation helix 16 is of a predetermined size and has only a short distal end portion thereof uninsulated. Those skilled in the art will know how to manufacture pacemaker leads, including the choice of materials to be used for the coil conductor 28 and the plastic covering therefore.

Figure 4:
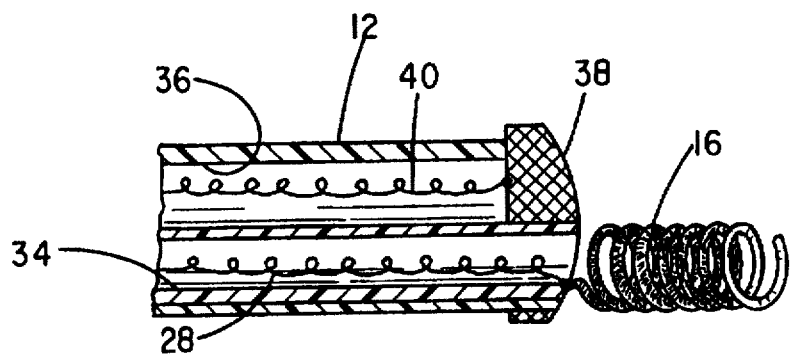
FIG. 4 is an enlarged, cross-sectioned, distal end view of a pacing lead of the type shown in FIG. 3, but in accordance with an alternative embodiment.

With a lead such as shown in FIG. 3 coupled to the pacemaker 36 and with the positive fixation tip 16 screwed into the interventricular septum 20 as illustrated in FIGS. 1 and 2, when cardiac stimulating pulses are generated by the pacemaker 36, the tissue comprising the myocardium of the left ventricle will be stimulated, resulting in left ventricular contraction. Because the more proximal convolutions of the rigid helix 16 are insulated, there will tend not to be a corresponding simultaneous depolarization of the right ventricle. If simultaneous depolarization of both the right and the left ventricles is desired, a lead having a positive fixation tip like that shown in FIGS. 1 and 2 can be used provided the insulating covering on the more proximal convolutions is not employed.

Where it is desired to pace both the right and the left ventricles at slightly different times, the lead illustrated in FIGS. 1–3 may be modified in the manner illustrated in FIG. 4. Here, the lead body 12 may comprise a tubular sheath having first and second lumens 34 and 36 where the lumen 34 is made to contain the elongated flexible conductor 28 that electrically connects to the conductive helix 16. Surrounding but insulated from the conductor 28 and the helix 16 is a conductive electrode 38 attached at the distal end of the lead body 12. The conductive electrode 38 preferably comprises a metal screen and a further flexible elongated conductor 40 passing through the lumen 36 electrically connects the screen electrode 38 to a second terminal pin (not shown) on the proximal end of the lead body 12.

When a lead having the construction like that illustrated in FIG. 4 is routed through the right atrium, the right ventricle and with the helix 16 being screwed into the interventricular septum 20, the screen electrode 38 will abut the right ventricular wall 24 of the septum to provide controlled electrical stimulation to that surface by a pulse which may be separated in time from the pulse applied to the left ventricle by the uninsulated convolutions at the distal end of the corkscrew tip 16.

In accordance with the method and apparatus of the present invention, it is contemplated that unipolar pacing of either or both of the right and left ventricles is involved and that the return electrode for each of the stimulating electrodes will be a surface of the metal can 40 that is exposed through an opening in a body compatible elastomeric insulating covering on the pacemaker 36. Alternatively, an additional ring electrode may be positioned proximal to the pacing tip of the lead body for bipolar pacing. There is disclosed in the prior art bipolar pacing leads having a stimulating tip electrode surrounding and insulated from a distally projecting positive fixation helix that is configured to cooperate with the tip electrode as a bipolar pair. However, the lead of the present invention differs therefrom in that it is designed to function in a unipolar mode and the tip geometry is such that when screwed into the interventricular septum, the electrode surface thereof stimulates the left ventricle without simultaneous stimulation of the right ventricle.

Figure 5:
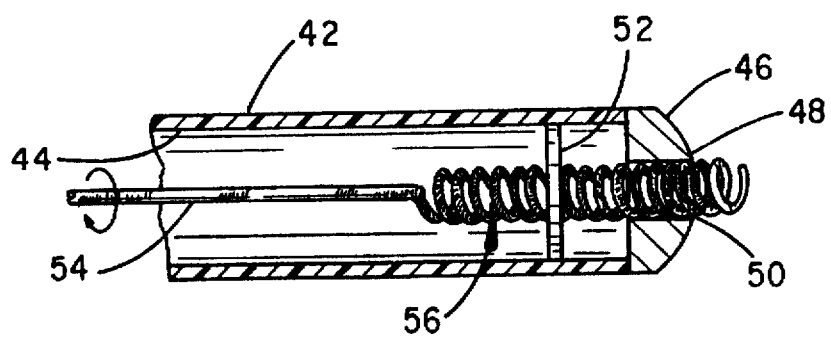
FIG. 5 is also an enlarged, cross-sectioned, partial view of a distal end portion of a pacing lead in accordance with a further embodiment of the invention.

FIG. 5 illustrates an alternative lead construction useful in effecting transeptal stimulation of the left ventricle. The pacing lead comprises an outer sheath 42 made from a suitable medical grade plastic, e.g., Silastic, defining a central lumen 44. Only the distal end portion of the alternative lead configuration is illustrated. Located at the distal end 46 of the tubular lead body is an insulating tip member 48 having a bore 50 formed longitudinally therethrough. Also disposed in the lumen 44 is a stationary, transversely oriented disk 52 having a small central aperture formed through its thickness dimension. A torqueable electrical conductor 54 is routed through the lumen 44 and it terminates in a helical or corkscrew tip indicated generally by numeral 56. As in the design depicted in FIG. 2, only one or so of the distalmost convolutions remain uninsulated while the remaining more proximal convolutions are coated with a suitable electrically insulating covering. The helical end portion 56 of the lead is threaded through the center aperture in the disk 52 such that when the torqueable conductor 54 is rotated in a clockwise direction, the helical end portion 56 of the lead will advance in the distal direction and out through the bore 50 formed in the lead tip 48.

With this construction, the positive fixation corkscrew tip can be fully retracted within the lead body 42 as the lead is routed through the vascular system and into the right ventricle of the heart. Now, by rotating the torqueable conductor 54, the corkscrew end portion is extended mechanically when the desired location where implantable is to take place has been reached. By further rotating the conductor 54, the coil 56 will be extended until capture of the left ventricle is verified by monitoring the morphology of a surface electrogram or an intracardial electrogram while either unipolar or bipolar stimulation is taking place. The electrogram may be sensed from the uninsulated helix tip to the pacer's can (assuming unipolar operation) or from the helix tip to a distally located ring electrode (not shown) when operating in a bipolar mode. When the helix tip is in the right ventricle tissue of the interventricular septum, two successive electrograms will appear similar to one another. When the tip is advanced into left ventricular tissue of the septum, a divergence will be noted in the two successive electrograms. In this fashion, the depth of penetration of the helix can be accommodated to septa of differing thicknesses and by monitoring the process, penetration of the tip through the septum into the left ventricle is avoided.

The present invention also provides a method for electrically stimulating the left ventricle of the heart which includes the steps of providing a cardiac pacemaker having a pulse generator, along with a pacing lead connected to the pulse generator output of the pacemaker where the lead includes a positive fixation, helically-wound electrode at its distal end whose length is only slightly less than the thickness of the heart's septum at a predetermined stimulation site. All but a predetermined number of distally located convolutions of the helically wound electrode are covered with an electrically insulating coating. At least a distal end portion of the pacing lead is surgically implanted in the right ventricle of the heart with the helically wound electrode being screwed into the heart's septum at the predetermined desired stimulation site so that the uninsulated distal tip portion of the helically wound electrode approaches, but does not penetrate, the left ventricle septal wall. The pulse generator is then used to apply stimulating pulses to the electrode via the pacing lead, so as to capture and effect contraction of the left ventricle without having a lead located in that ventricle.

This invention has been described herein in considerable detail in order to comply with the Patent Statutes and to provide those skilled in the art with the information needed to apply the novel principles and to construct and use such specialized components as are required. However, it is to be understood that the invention can be carried out by specifically different equipment and devices, and that various modifications, both as to the equipment details and operating procedures, can be accomplished without departing from the scope of the invention itself.

What is claimed is:

1. A method for electrically stimulating the left ventricle of the heart from a site within the right ventricle, comprising the steps of:
   (a) providing a cardiac pacemaker having a pulse generator producing stimulating pulses;
   (b) providing a unipolar pacing lead comprising an elongated, flexible, body-compatible, plastic sheath covering an elongated electrical conductor, the conductor including a terminal at a proximal end thereof for connection to the cardiac pacemaker and a positive-fixation, helically-wound electrode at a distal end thereof of a length that is only slightly less than the thickness of the heart's septum at a predetermined desired stimulation site within the right ventricle and with all but a predetermined number of distally located convolutions of the helically wound electrode being covered with an electrically insulating coating;
   (c) surgically implanting at least a distal end portion of the pacing lead in the right ventricle of the heart with the helically wound electrode being screwed into the heart's septum at the predetermined desired stimulation site so that an uninsulated distal tip portion of the helically wound electrode resides in myocardial tissue of the left ventricle, but does not penetrate, the left ventricle septal wall;
   (d) coupling the terminal of the conductor to the pacemaker pulse generator; and
   (e) applying stimulating pulses to the electrode via the pacing lead for evoking depolarization of the myocardial tissue of the left ventricle.

2. The method as in claim 1 wherein the helically wound electrode is retractable and extendible relative to a distal end of said sheath.

3. A method for selectively electrically stimulating both the left and right ventricles of the heart, either simultaneously or with a predetermined delay in between using a single pacing lead, comprising the steps of:
   (a) providing a cardiac pacemaker having a pulse generator producing pulses at timed intervals;
   (b) providing a pacing lead comprising an elongated, flexible, body-compatible, plastic sheath covering a pair of elongated electrical conductors, the conductors being insulated from one another and each including a terminal at a proximal end thereof for connection to the cardiac pacemaker and one conductor of the pair having a positive-fixation, helically-wound electrode projecting outwardly at a distal end of the sheath with all but a predetermined number of distally located convolutions of the helically wound electrode being covered with an electrically insulating coating and a further electrode affixed to the distal end of the sheath and electrically isolated from the helically-wound electrode and connected to the other conductor of the pair;
   (c) surgically implanting at least a distal end portion of the pacing lead in the right ventricle of the heart with the helically wound electrode being screwed into the heart's septum at the predetermined desired stimulation site so that an uninsulated distal tip portion of the helically wound electrode resides in myocardial tissue of the left ventricle, but does not penetrate, the left ventricle septal wall and with the further electrode contacting right ventricular septal tissue;
   (d) coupling the terminals of the pair of conductors to the pacemaker pulse generator; and
   (e) applying stimulating pulses to the electrodes via the pacing lead for evoking selective depolarization of the myocardial tissue of the right and left ventricles.

4. The method as in claim 3 wherein the helically-wound electrode is extendible and retractable relative to the distal end of the sheath and stimulating pulses are applied to the helically wound electrode as the helically wound electrode is advanced into the heart's septum.

5. The method as in claim 4 and further including the step of sensing right and left ventricular depolarization resulting when the stimulating pulses are applied to the helically wound electrode as the helically wound electrode is advanced into the heart's septum and terminating advancement of the helically wound electrode when left ventricular depolarization is sensed prior to right ventricular depolarization.

* * * * *